United States Patent
Warntjes

(10) Patent No.: US 8,874,189 B2
(45) Date of Patent: *Oct. 28, 2014

(54) METHOD OF VISUALIZING MR IMAGES

(75) Inventor: Marcel Warntjes, Linköping (SE)

(73) Assignee: SyntheticMR AB, Linköping (SE)

( * ) Notice: Subject to any disclaimer, the term of this patent is extended or adjusted under 35 U.S.C. 154(b) by 873 days.

This patent is subject to a terminal disclaimer.

(21) Appl. No.: 12/521,903

(22) PCT Filed: Dec. 21, 2007

(86) PCT No.: PCT/SE2007/001145
§ 371 (c)(1),
(2), (4) Date: Jul. 1, 2009

(87) PCT Pub. No.: WO2008/082341

PCT Pub. Date: Jul. 10, 2008

(65) Prior Publication Data

US 2010/0103166 A1    Apr. 29, 2010

Related U.S. Application Data

(60) Provisional application No. 60/939,116, filed on May 21, 2007, provisional application No. 60/912,476, filed on Apr. 18, 2007, provisional application No. 60/883,129, filed on Jan. 2, 2007.

(51) Int. Cl.
*A61B 5/055* (2006.01)
*G06T 7/00* (2006.01)
*A61B 5/00* (2006.01)
*G09G 5/00* (2006.01)
*G01R 33/56* (2006.01)

(52) U.S. Cl.
CPC .......... *G06T 7/0012* (2013.01); *G01R 33/5602* (2013.01); *A61B 5/055* (2013.01); *A61B 5/7445* (2013.01); *G01R 33/5608* (2013.01); *A61B 5/0037* (2013.01); *A61B 5/0042* (2013.01)
USPC ............................ 600/410; 345/617; 382/131

(58) Field of Classification Search
USPC ............................ 345/617; 382/131; 600/410
See application file for complete search history.

(56) References Cited

U.S. PATENT DOCUMENTS 4,634,979 A  1/1987  Riederer et al.
4,641,095 A  2/1987  Riederer (Continued)

FOREIGN PATENT DOCUMENTS

DE  102005027483 B3  12/2006
EP  1136836 A2  9/2001

OTHER PUBLICATIONS

PCT International Search Report, mailed Apr. 24, 2008, in connection with International Application No. PCT/SE2007/001145.

(Continued)

*Primary Examiner* — Long V. Le
*Assistant Examiner* — Angela M Hoffa
(74) *Attorney, Agent, or Firm* — Piedmont Intellectual Property

(57) ABSTRACT

In a method and a device MR images having various contrasts are scanned and then values for some or all of the parameters T1, T2 and PD related to the scanned MR images are determined. Based on the scanned MR images and the determined parameter values an initial conventional MR contrast image with some default scanner settings is generated, or alternatively, a stronger non-physical MR contrast image. The initial MR contrast image can then be manipulated by a user in response to movement of a user-controlled marker on a screen showing the contrast image such that a contrast optimized image can be obtained for a particular diagnosis in a very short time. Furthermore a quantitative image can be generated representing the amount of a single tissue type.

35 Claims, 4 Drawing Sheets

(56) References Cited

U.S. PATENT DOCUMENTS

| | | | |
|---|---|---|---|
| 4,881,033 A | 11/1989 | Denison et al. | |
| 5,262,945 A | 11/1993 | DeCarli et al. | |
| 5,486,763 A | 1/1996 | Alfano | |
| 6,366,797 B1 | 4/2002 | Fisher et al. | |
| 6,823,205 B1 | 11/2004 | Jara | |
| 6,888,350 B2* | 5/2005 | Deimling | 324/309 |
| 6,917,199 B2 | 7/2005 | Jara | |
| 7,002,345 B2 | 2/2006 | Jara | |
| 7,280,681 B2* | 10/2007 | Meyer | 382/128 |
| 7,570,051 B2* | 8/2009 | Haider | 324/307 |
| 7,973,530 B2* | 7/2011 | Warntjes | 324/309 |
| 8,228,063 B2* | 7/2012 | Kimura | 324/309 |
| 8,289,329 B2* | 10/2012 | Warntjes | 345/440 |
| 2002/0183614 A1 | 12/2002 | Feiweier et al. | |
| 2003/0092981 A1 | 5/2003 | Deimling | |
| 2003/0095147 A1 | 5/2003 | Daw | |
| 2004/0169512 A1* | 9/2004 | Jara | 324/309 |
| 2004/0227514 A1* | 11/2004 | Jara | 324/310 |
| 2007/0167727 A1 | 7/2007 | Menezes et al. | |
| 2007/0247157 A1 | 10/2007 | Haider | |
| 2007/0276221 A1* | 11/2007 | Warntjes | 600/410 |
| 2009/0267599 A1* | 10/2009 | Warntjes | 324/307 |
| 2009/0267945 A1* | 10/2009 | Warntjes | 345/440 |
| 2010/0127704 A1* | 5/2010 | Warntjes | 324/309 |
| 2011/0018537 A1 | 1/2011 | Warntjes | |

OTHER PUBLICATIONS

Warntjes, J.B.M et al.: "Method for rapid, whole vol. T1, T2* and Proton Density quantification" Magn Reson Med, accepted Nov. 10, 2006.

Neeb, H. et al.: "A new method for fast quantitative mapping of absolute water content in vivo" NeuroImage 2006; 31:1156-1168.

Deoni, S.C.L et al.: "High resolution T1 and T2 mapping of the brain in a clinically acceptable time with DESPOT1 and DESPOT2" Magn Reson Med 2005;53:237-241.

Zhu, X.P. et al.: "Magnetic resonance image synthesis using a flexible model." Br J Radiol 1994;67:976-982.

Gulani, V. et al.: "Towards a single-sequence neurologic magnetic resonance imaging examination: multiple-contrast images from an IR TrueFISP experiment." Invest Radiol 2004;39:767-774.

PCT International Preliminary Report on Patentability, mailed Jul. 16, 2009, in connection with International Application No. PCT/SE2007/001145.

R. Maitra et al., Bayesian Reconstruction in Synthetic Magnetic Resonance Imaging, Proc. SPIE, 1998, pp. 39-47, vol. 3459.

M. Prastawa et al., Synthetic Ground Truth for Validation of Brain Tumor MRI Segmentation, Med Image Comput Comput Assist Interv., 2005, pp. 26-33, 8 (Pt 1).

K.H. Cheng et al., In-vivo Tissue Characterization of Brain by Synthetic MR Proton Relaxation and Statistical Chisquares Parameter Maps, Proc. 8th Symposium on Computer-Based Medical Systems, 1995, pp. 338-345, IEEE.

M. Warntjes et al., Rapid Magnetic Resonance Quantification on the Brain: Optimization for Clinical Usage, Magnetic Resonance in Medicine, 2008, pp. 320-329, vol. 60, Wiley-Liss, Inc.

B. Grassiot et al., Quantification and Clinical Relevance of Brain Atrophy in Multiple Sclerosis: A Review, J. Neurol., 2009, pp. 1397-1412, vol. 256, Springer.

J. West et al., Novel Whole Brain Segmentation and Volume Estimation Using Quantitative MRI, Eur. Radiol., Nov. 24, 2011, pp. 1-10, Springer.

* cited by examiner

METHOD OF VISUALIZING MR IMAGES

TECHNICAL FIELD

The present invention relates to a method and a device for visualizing magnetic resonance (MR) images.

BACKGROUND

Magnetic Resonance Imaging (MRI) can generate cross-sectional images in any plane (including oblique planes). Medical MRI most frequently relies on the relaxation properties of excited hydrogen nuclei in water and fat. When the object to be imaged is placed in a powerful, uniform magnetic field the spins of the atomic nuclei with non-integer spin numbers within the tissue all align either parallel to the magnetic field or anti-parallel. The output result of an MRI scan is an MRI contrast image or a series of MRI contrast images.

In order to understand MRI contrast, it is important to have some understanding of the time constants involved in relaxation processes that establish equilibrium following RF excitation. As the high-energy nuclei relax and realign, they emit energy at rates which are recorded to provide information about their environment. The realignment of nuclear spins with the magnetic field is termed longitudinal relaxation and the time (typically about 1 sec) required for a certain percentage of the tissue nuclei to realign is termed "Time 1" or T1. T2-weighted imaging relies upon local dephasing of spins following the application of the transverse energy pulse; the transverse relaxation time (typically <100 ms for tissue) is termed "Time 2" or T2. On the scanner console all available parameters, such as echo time TE, repetition time 0, flip angle $\alpha$ and the application of preparation pulses (and many more), are set to a certain value. Each specific set of parameters generates a particular signal intensity in the resulting images depending on the characteristics of the measured tissue.

Image contrast is then created by using a selection of image acquisition parameters that weights signal by T1, T2 or no relaxation time PD ("proton-density images"). Both T1-weighted and T2-weighted images as well as PD images are acquired for most medical In contrast imaging the absolute signal intensity observed in the image has no direct meaning; it is rather the intensity difference, the contrast, between different tissues that lead to a diagnosis. The TE, TR, $\alpha$ and pre-pulses are chosen such that it provides the best contrast for a specific application. This implies that for each desired contrast a separate image has to be taken. This in turn will make a complete examination rather time consuming and demanding for the patient. Also, it will become costly since equipment and other resources can only be used for one patient at the time. If the known parameter settings do not provide the desired contrast, insufficient for diagnosis, it is far from straightforward to achieve an improvement.

SUMMARY

It is an object of the present invention to overcome or at least reduce some of the problems associated with existing method for visualizing data obtained in an MRI scan.

It is another object of the present invention to provide a method and a device that reduces the time required for an individual examination utilizing MRI, thereby freeing up resources.

It is another object of the present invention to visualize patient tissue in a much stronger manner than conventional imaging systems are capable of.

These object and others are obtained by a method and a device as set out in the appended claims and adapted to display synthesized Magnetic Resonance (MR) contrast images where MR contrast and/or image Signal to Noise Ratio (SNR) is automatically optimized by means of one or several specific user-interactive events.

Hence, by first scanning MR images having various contrast and then computing values for some or all of the parameters T1, T2 and PD related to the scanned MR images, an initial MR contrast image with some default scanner settings can be generated. The initial MR contrast image can then be manipulated by a user in response to movement of a user-controlled marker a screen showing the contrast image such that a contrast optimized image can be obtained for a particular diagnosis in a very short time.

In accordance with the present invention it is possible to show the user a synthesized MR image based on previously acquired scans where the user is enabled to choose optimal $T_1$, $T_2$ or PD contrast and also is enabled to use particular pre-pulses.

In accordance with another aspect of the present invention a user is enabled to select a single Region of Interest (ROI) within a synthesized image for which the optimal contrast is calculated or to view a synthesized image where the optimal contrast difference between several Regions of Interest is calculated.

In accordance with the present invention any scanner setting can be chosen with the corresponding contrast once the tissue characteristics are measured. In practice this means that the patient will undergo a single quantification scan after which any desired contrast image can be reconstructed in post-processing at any time after the examination. Hence it will be possible to automatically synthesize the most optimal contrast images based on only a limited input of the user, which will save time and resources. The method of synthesizing contrast image can advantageously be implemented in computer software and stored on a computer program product.

In accordance with another aspect of the present invention the quantitative nature of the MR measurement is used to automatically highlight or suppress a single tissue type. Each tissue has its own unique combination of MR tissue parameters which is utilized to selectively visualize one or more tissues while suppressing all others. Hereby it is possible to single out a particular type of tissue and display the tissue type in a clear way. In accordance with one embodiment the visualization of a particular type of tissue is automated such that similar tissue as underneath a region of interest automatically lights up or vanishes from a displayed image.

In accordance with yet another aspect of the present invention a direct correspondence of the value of each tissue parameter to a basis color value is utilized. Since each tissue has its own unique set of three MR tissue parameters (T1, T2, PD) it will be possible to display as a unique color composition of three basis colors, or a subset thereof. The color transfer functions can be visualized and updated in another panel. It is not necessary that each tissue parameter value is linked to a visible color. For example it is possible to set ranges for the values to display. Outside these ranges the tissue will not be visible on the synthetic MR color image.

In addition to this a region of interest might be visualized on the image where only other pixels with similar tissue parameters are updated or shown. This will be helpful in segmentation of tissue. More ROIs may be displayed to highlight several tissues simultaneously. The MR color images are ideally displayed in combination with variable color transparency, volume rendering and/or 3D visualization.

BRIEF DESCRIPTION OF THE DRAWINGS

The present invention will now be described in more detail by way of non-limiting examples and with reference to the accompanying drawings, in which.

DETAILED DESCRIPTION

Figure 1:
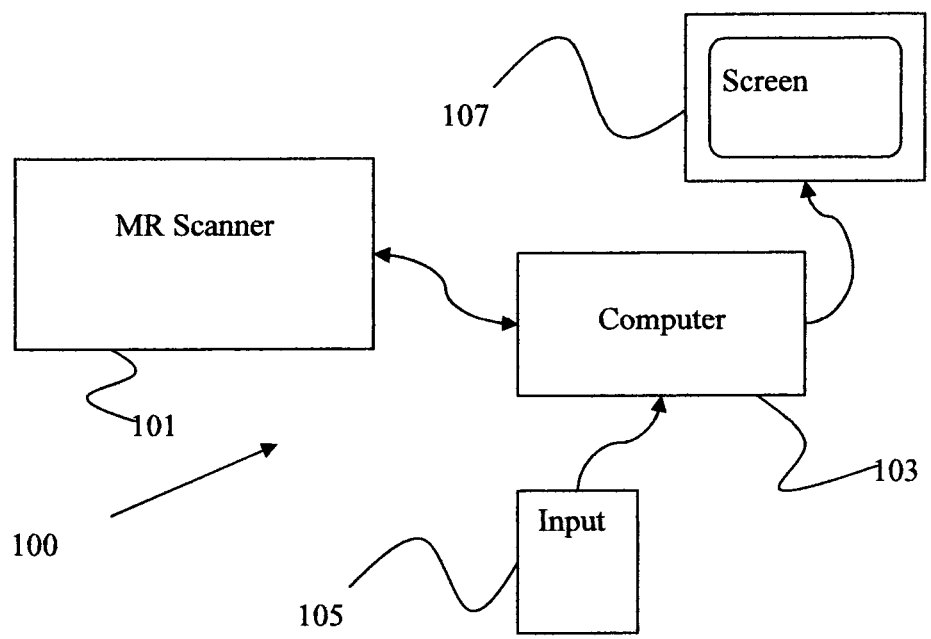
FIG. 1 is a general view of a MRI system.

In FIG. 1 a general view of a setup of a MRI system 100 is depicted. The system 100 comprises a MR scanner 101. The MR scanner is operative to generate MRI data by means of scanning a living object. The MR scanner is further connected to a computer 103 for processing data generated by the scanner 101. The computer comprises a central processor unit coupled to a memory and a number of input and output ports for receiving and outputting data and information. The computer 103 receives input commands from one or several input devices generally represented by an input device 105. The input device may be one or many of a computer mouse, a keyboard, a track ball or any other input device. The computer 103 is further connected to a screen 107 for visualizing the processed scanner data as a contrast image.

Figure 2:
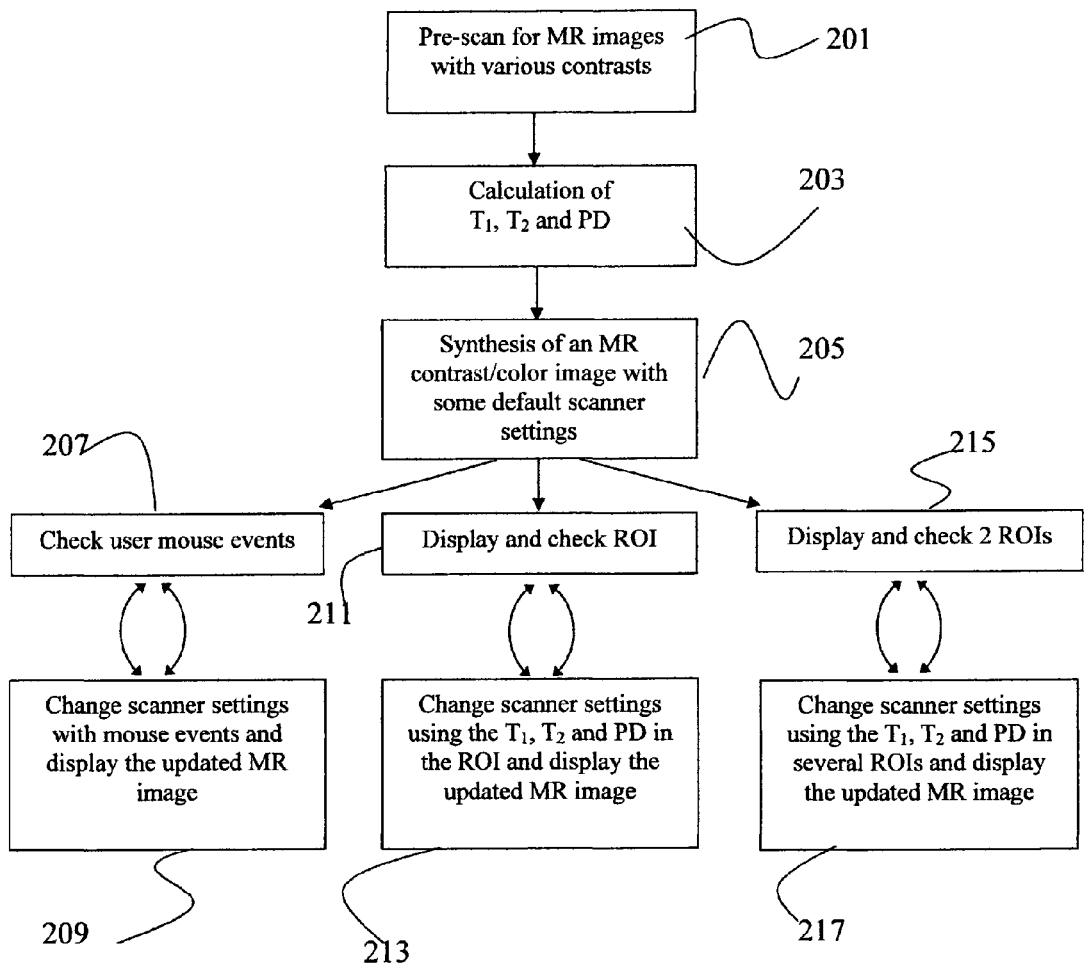
FIG. 2 is a flowchart illustrating steps performed when generating contrast images.

In FIG. 2, a flowchart illustrating steps performed when generating contrast images is shown. First in a step 201 a pre-scan is performed to acquire several MR images of a patient with various contrasts. Next, in a step 203 the images generated in step 201 are used to determine the patient specific $T_1$ relaxation time, the $T_2$ relaxation time and the Proton Density (PD), or for some applications a subset thereof. The method for determining the patient specific $T_1$ relaxation time, $T_2$ relaxation time and Proton Density (PD) can be any suitable method. However it is preferred to use a fast method to reduce the overall time of an examination. Examples of fast pre-scan methods are described in: Warntjes J B M, Dahlquist O, Lundberg P. Method for rapid, whole volume $T_1$, $T_2^*$ and Proton Density quantification. Magn Reson Med, accepted 2006 Nov. 10.; Neeb H, Zilles K, Shah N J. A new method for fast quantitative mapping of absolute water content in vivo. NeuroImage 2006; 31:1156-1168; and Deoni S C L, Rutt B K, Peters T M. High resolution $T_1$ and $T_2$ mapping of the brain in a clinically acceptable time with DESPOT1 and DESPOT2. Magn Reson Med 2005; 53:237-241.

Using the pre-scan information any MR contrast image can be synthesized. This is because the intensity in the synthesized contrast images is a function of the patient specific parameters as well as freely chosen MR scanner parameters such as echo time (TE), repetition time (TR), RF flip angle and inversion pulse delay time TI. Equations for the calculation of the expected intensity can be found in Haacke, E M, Brown R W, Thompson M R, Venkatesan R. Magnetic Resonance Imaging, physical principles and sequence design. ISBN 0-471-35128-8 J. Wiley & Sons. Practical examples of methods for contrast image synthesis are described in Gulani V, Schmitt P, Griswold M, Webb A G, Jakob P M. Towards a single-sequence neurologic magnetic resonance imaging examination: multiple-contrast images from an IR TrueFISP experiment. Invest Radiol 2004:39; 767-74. and Zhu X P, Hutchinson C E, Hawnaur J M, Cootes T F, Taylor C J, Isherwood I. Magnetic resonance image synthesis using a flexible model. Br J Radiol 1994:67; 976-82.

Next, in a step 205, an arbitrary initial MR contrast image is synthesized using some default scanner parameter settings as a starting point for generating such an initial contrast image. The image generated in step 205 will be very similar to a conventional contrast image. Using the default initial contrast image as a starting point a user operating the MR visualizing system as described herein has a number of different options to manipulate the synthesized contrast image displayed on the screen as will be described hereinafter.

In accordance with a first option, when the computer is set to operate in a first mode 207, the user may want to change the weight of $T_1$ weighted contrast in the displayed synthesized MR image. In response to such an indication for example the computer may be configured to interpret a horizontal mouse movement as such an indication the value of TR, TI and/or flip angle in the scanner settings are changed by the computer, leading to an apparent change of $T_1$ weighted contrast in the displayed synthesized MR image. In a corresponding manner the computer can be configured to interpret, also given as an example, a vertical mouse movement as a change of the value of TE, leading to an apparent change of $T_2$ weighted contrast in the displayed synthesized MR image. The change of contrast is performed in a step 209.

In accordance with a second option, when the computer is set to operate in a second mode 211, the computer can be configured to interpret a movement of an indication of a Region Of Interest (ROI) in the displayed synthesized MR image as a request for an automatic change of scanner settings for the displayed synthesized MR image, depending on the $T_1$, $T_2$ and PD inside the ROI. In response to such a request the computer determines the requirement for the updated scanner settings satisfy some pre-determined condition in a step 213. For example, the condition may advantageously by the optimal inversion delay time TI for zero intensity inside the ROI resulting in that the ROI area is visualized as black on the screen or the optimal setting for TR and flip angle for the highest SNR.

In accordance with the second option, the complete image changes contrast as soon as the user moves or changes his ROI in order to keep the average of the ROI optimal. A good example of when this option can be utilized is the so-called late-enhancement method where a $T_1$ contrast agent is administered to a patient with suspected myocardial infarction. After 10-20 minutes ischemic myocardium shows a higher contrast agent concentration and hence a lower $T_1$ value than healthy myocardium. An inversion recovery sequence is then performed in order to try to display the healthy tissue as black and the ischemic tissue as bright. The contrast in the image depends critically on the delay time between the inversion pulse and the actual measurement. Using conventional methods, finding the correct inversion delay time may take an experienced operator up to 10 minutes.

If, however, the value of $T_1$ is known and the image can be reconstructed based on quantification, the scanner parameters, in this case mostly the inversion delay time, are optimized such that the tissue in the ROI appears black. Automatically ischemic tissue turns bright.

As an example for the reconstruction of intensity images based on the quantification scans a simple spin echo sequence can be reconstructed as follows. The intensity I of each pixel in the image is a function of the scanner parameters echo time TE, repetition time TR, and the flip angle α and simultaneously a function of tissue characteristics such as $T_1$ relaxation, $T_2$ relaxation and proton density PD:

$$I \propto PD\exp(-TE/T_2)\sin\alpha \frac{1-\exp(-TR/T_1)}{1-\exp(-TR/T_1)\cos(\alpha)} \quad (1)$$

Knowing the tissue characteristics it is possible to reconstruct the images with any desired scanner settings. This can be extended to include preparation pulses (e.g. inversion or saturation), multi-shots (turbo factors) and various timings (as with multi slice sequences). If the tissue characteristics are known in 3D any slice thickness and orientation can be chosen. It might even improve the original image quality because no additional image artifacts will be introduced such as eddy currents, ghosting or flow artifacts.

Another example is the calculation of the expected intensity after an inversion pre-pulse of a gradient echo sequence as used in the late enhancement example: The saturated magnetization $M_0^*$ during the measurement can then be calculated as:

$$M_0^* = M_0 \frac{1-\exp(-TR/T_1)\cos(\alpha)^{TFE} + \exp((-TR+T_{inv})/T_1)\cdot(\cos(\alpha)^{TFE}-1)}{1-\exp(-TR/T_1)\cos(\theta)\cos(\alpha)^{TFE}} \quad (2)$$

where the unsaturated magnetization $M_0$ is proportional to PD, TFE is the number of Turbo Field Echo shots and $T_{inv}$ is the inversion delay time after the inversion pulse θ. Subsequently the intensity at a particular inversion delay time $T_{inv}$ is calculated as:

$$I \propto \exp(-TE/T_2^*)\sin(\alpha)[M_0-(M_0+M_0^*)\exp(-T_{inv}/T_1)] \quad (3)$$

where $T_2$ is replaced by $T_2^*$ relaxation since it is a gradient echo sequence instead of a spin echo sequence. Similar equations can be derived for any other contrast.

In accordance with a third option, when the computer is set to operate in a third mode 215, the movement of two indications of Regions Of Interest in the displayed synthesized MR image can be set to result in an automatic change of scanner settings for the displayed synthesized image, depending on the $T_1$, $T_2$ and PD inside the two ROIs as indicated in step 217. The computer when operating in this third mode can advantageously be configured to set the scanner settings such that it matches the criteria of optimizing intensity difference between the two ROIs marked on the screen.

An example illustrating when the display of multiple ROIs in the reconstructed image to optimize the contrast between the ROIs is the imaging of the brain where the contrast between grey and white matter is optimized by placing one ROI on the white matter and one ROI on the grey matter. Possible choices are to optimize TI, TR and α for $T_1$ contrast or TE for $T_2$ contrast. Simultaneously the Signal to Noise ratio in the synthesized imaged can be optimized as well.

Using the equations as set out above in conjunction with the description of the operation of the computer when in the third mode will also allow for calculation of the largest intensity difference between various tissues with different tissue characteristics. The general $T_1$, $T_2$ and PD become tissue specific $T_{1a}$, $T_{2a}$ and $PD_a$ for tissue a, $T_{1b}$, $T_{2b}$ and $PD_b$ for tissue b etc. For two ROIs the largest intensity difference for $T_1$ contrast can be found by varying TR and α, for $T_2$ contrast TE can be changed. An optimum can then be found using the general formula $$(I_a-I_b)'=0$$

where the prime denotes the derivative to any variable.

In another embodiment of the present invention the synthesis of conventional contrast images can be enhanced by modifying the intensity equations (Eq. 1-3). For example, the normalization of the PD parameter can be set such that the measured proton density appears to be uniform over the image. A T1 weighted image will then be purely T1 weighted without the counteracting proton density contrast.

In accordance with another embodiment the influence of T1 on the image intensity can be inverted, e.g. by using $$I \propto PD\exp(-TE/T_2)\sin(\alpha)\exp(-TE/T_1)$$

for the synthesis. This will enhance T2 weighted imaging owing to additional T1 weighting.

It is not necessary to visualize the obtained T1, T2 and PD parameters as conventional contrast images. Instead, non-physical but much stronger contrasts can be used. The three parameters can be taken as coordinates in a three-dimensional space where T1, T2 and PD, or a function of T1, T2 and PD, serve as axes (x,y,z). In such a space similar tissue will form a cluster of coordinates. Since the MR measurement is quantitative, clusters will always appear at the same position inside this space. Vectors can be defined as $$(x,y,z)=((W_{T1}(T_1-T_{1,0})),(W_{T2}(T_2-T_{2,0})),(W_{PD}(PD-PD_0)))$$

where $T_{1,0}$, $T_{2,0}$, $PD_0$ is a defined origin in T1-T2-PD space and $W_{T1}$, $W_{T2}$, $W_{PD}$ are the weights of the vector elements.

An exemplary function that can be used on T1 and T2 is the inverse, in order to obtain the relaxation rates R1=1/T1 and R2=1/T2. Using relaxation rates the weighted vector combination becomes:

$$(x,y,z)=((W_{R1}(R_1-R_{1,0})),(W_{R2}(R_2-R_{2,0})),(W_{PD}(PD-PD_0)))$$

where $R_{1,0}$, $R_{2,0}$, $PD_0$ is a defined origin in R1-R2-PD space and $W_{R1}$, $W_{R2}$, $W_{PD}$ are the weights of the parameters.

The origin of such a vector can be placed in the center of a first tissue cluster and the normalized distance can be calculated with respect to all other tissue clusters. Inside the R1 R2 PD space this value would correspond to a partial volume of the first tissue type in relation with the others. Images can therefore be synthesized to display the relative amount of a certain tissue type between 0 and 100%. Integration of such an image results in the absolute volume of that tissue inside the displayed slice. A reference table can be set up to pre-define the origin locations of specific tissue types.

A clinical application for the brain of such synthetic vector imaging is display of a 'white matter image', a 'grey matter image' and a 'CSF image' on a scale between 0 and 100%. This can be used to quantify for example brain atrophy.

In accordance with another embodiment, the display of an image of the brain where all tissue is set to 1. Subsequently the aforementioned 'white matter image', 'grey matter image' and 'CSF image' are subtracted. The resulting non-WM/GM/CSF image can be used to show a 'disease image' containing the relative amount of tissue that is not recognized as WM, GM or CSF. This technique is sensitive for the detection of e.g. Multiple Sclerotic lesions or the excess amount of water in case of oedema.

Other clinical applications are the specific suppression of fat in the images or the specific enhancement of blood vessels (angio). In these cases images can be displayed where a single tissue cluster is suppressed or enhanced. The cluster can be selected by placing the origin at the center and defining a 3D width in space.

The synthetic vector images can be generated automatically by displaying a region of interest on the synthetic image where the origin of the vector is automatically located at the tissue cluster underneath the ROI. The intensity in the image will automatically be set to correspond to the absolute distance (vector length) from the origin.

Another example is the display of two regions of interest where one region (hence cluster) is set to black and the other region (hence cluster) set to white. All other coordinates in the space are automatically set to a grey value corresponding to e.g. the ratio of the absolute distance to one cluster and the absolute distance to the second cluster.

In accordance with another embodiment of the present invention each MR tissue parameter is associated with a color. For example in an RGB (Red, Green, Blue) coded image each MR tissue parameter is linked to one of the colors Red, Green or Blue. Since each tissue has its own unique set of three MR tissue parameters (T1, T2, PD) it will be possible to display as a unique color composition of three basis colors (or a subset thereof). The color transfer functions can be visualized and updated in another panel. It is not necessary that each tissue parameter value is linked to a visible color. Hence it is possible to set ranges for the values to display. Outside these ranges the tissue will not be visible on the synthetic MR color image.

In addition to this a region of interest might be visualized on the image where only other pixels with similar tissue parameters are updated or shown. This will be helpful in segmentation of tissue. More ROIs may be displayed to highlight several tissues simultaneously. The MR color images are ideally displayed in combination with variable color transparency, volume rendering and/or 3D visualization. The steps performed when generating a color coded image as set out above will be similar to the steps performed when generating a contrast image as described above in conjunction with FIG. 2.

Figure 3:
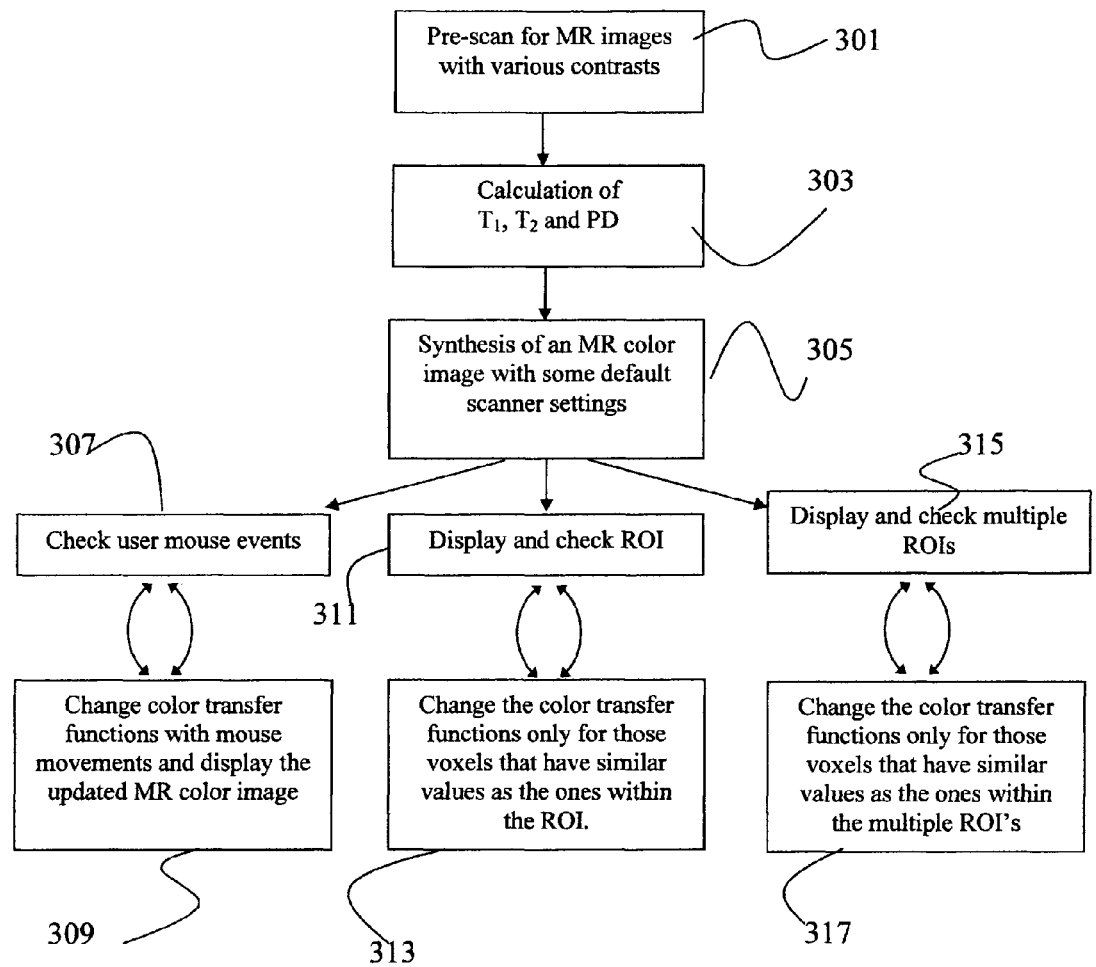
FIG. 3 is a flowchart illustrating steps performed when generating a color coded image.

In FIG. 3 a flow chart illustrating steps performed when generating a color coded image is shown. Hence, first in a step 301 a pre-scan is performed to acquire several MR images of a patient with various contrasts. Next, in a step 303 the images generated in step 301 are used to determine the patient specific $T_1$ relaxation time, the $T_2$ relaxation time and the Proton Density (PD), or for some applications a subset thereof.

Thereupon, in a step 305, a color coded image is generated. The correspondence between an absolute MRI parameter the amount of color or opacity and color palette itself are free to choose. By way of example, the value of the absolute $T_1$ relaxation time can be set to determine the amount of red. For example values of 200-2000 ms correspond linearly with 0-255 of red. The value of the absolute $T_2$ relaxation time can similarly be set to determine the amount of green. For example values of 200-500 ms correspond linearly with 0-255 of green. Finally the value of the absolute proton density can be set to determine the amount of blue. For example values of 200-1000 ms correspond linearly with 0-255 of blue. Tissue with $T_1$=2000, $T_2$=500 and PD=1000 would then appear white (=255, 255, 255) in the color coded image.

The color coded image generated in step 305 can then be manipulated in a manner similar to the contrast image generated in step 205 above. Thus, in response to different input device movements, such a computer mouse movement, the color transfer function may be altered. Thus if in a first mode, a computer mouse is moved in one direction, in a step 307, the generated and displayed color coded image is displayed using another color coding transfer function, step 309. The change in color coding transfer function is then set to correspond to the computer mouse movement. For example by moving the computer mouse in one direction the midpoint of the color scale may be altered whereas moving the computer mouse in another direction may be set to correspond to a change in the range of the color scale. In the example given above where the $T_1$ relaxation time is set to determine the amount of red and where values of 200-2000 ms correspond linearly with 0-255 of red in the initial image, a movement in one direction may be set to alter the lover value in the time range and a movement in another direction may correspond to a change of the upper value in the range. Hence, if the user is interested in the range 1600-1800 ms such a range can easily be set to correspond linearly with 0-255 of red.

In a second mode, if in a step 311 an ROI is selected, the color coding transfer function is set to only be changed in response to user manipulation for those voxels having similar properties as the voxels within the selected ROI, step 313. Also is in a third mode, if more than one ROI is selected, in a step 315, the color coding transfer function is set to be changed in response to user manipulation only for voxels having properties similar to the voxels inside the selected ROIs, step 317.

Furthermore it is also possible to combine visualization of the procedures described above in conjunction with FIG. 2 and FIG. 3. Thus, in such a combined visualization scheme contrast and color can be manipulated side by side or simultaneously by a user. The transfer function will then be adapted to both perform contrast variations and color variation in response to user input.

The methods and systems described above quantify the absolute MR tissue parameters (T1, T2, and PD). Subsequently, using a direct correspondence of the values of these parameters in combination with chosen values of the MR scanner settings (TE, TR, α, pre-pulses) images can be visualized in a manner similar ordinary MR contrast images.

However, it is not necessary to display a physically possible contrast image, i.e. one that can be obtained using conventional methods for obtaining MR contrast images. An example of a non-physical contrast image that is of high diagnostic value is the proton density normalized image. This is a synthetic contrast image where the proton density of all tissues has been set to the same value. This way the ever-present proton contrast has been removed from the contrast image and a pure T1-weighted or a pure T2-weighted image can be visualized. This is not possible to display other than by using synthetic MRI MR signal intensity can be split up into three components, each component depending on PD, T2 and T1, respectively. An example is the expected intensity of a normal spin echo sequence:

$$I \propto PD \exp(-TE/T_2) \sin(\alpha) \frac{1 - \exp(-TR/T_1)}{1 - \exp(-TR/T_1)\cos(\alpha)}$$

where TE is the echo time, TR is the repetition time and α is the RF flip angle.

There is no MR sequence that can vary the contribution of PD in this equation. Using absolute quantification PD can be set to any arbitrary value. Especially the pure T1-weighted image is important since PD gives a positive contribution to the intensity and T1 gives a negative contribution thus resulting in that the two components counteract each-other.

Figure 4:
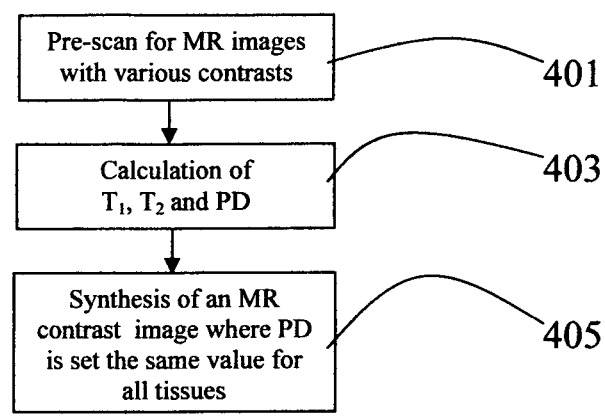
FIG. 4 is a flowchart illustrating steps performed when generating a non-physical MR image.

In FIG. 4, a flow chart illustrating different steps performed when generating a non-physical MR image. First in a step 401 a pre-scan is performed to acquire several MR images of a patient with various contrasts. Next, in a step 403 the images generated in step 401 are used to determine the patient specific $T_1$ relaxation time, the $T_2$ relaxation time and the Proton Density (PD), or for some applications a subset thereof. The method for determining the patient specific $T_1$ relaxation time, $T_2$ relaxation time and Proton Density (PD) can be any suitable method. Finally, in a step 405, a synthesized image where the PD value is set to the same value for all tissues is generated and displayed. Hereby a PD normalized image is obtained which will provide an enhanced view of in particular T1 weighted images.

Using the method and device as described herein a patient undergoing a medical examination will only undergo a single quantification scan after which any desired contrast image can be reconstructed in post-processing at any time after the examination. Hence it will be possible to automatically synthesize the most optimal contrast images based on only a limited input of the user, which in turn will save time and resources. The method can suitably be implemented using computer software adapted to be executed on a computer.

The invention claimed is:

1. A method of visualizing magnetic resonance (MR) images on a screen, the method comprising the steps of:
    scanning MR images having various contrast,
    computing values for the parameters T1 relaxation time, T2 relaxation time, and proton density (PD) for the scanned MR images or a subset of those parameters, the subset including at least one of each of T1 relaxation time, T2 relaxation time, and proton density PD,
    generating an MR contrast image using the scanned MR images, computed values, and a set of default scanner settings, and
    adjusting the image contrast of said MR contrast image by changing scanner settings in response to a user-controlled marker on said screen.

2. The method according to claim 1, wherein said user-controlled marker represents a region of interest (ROI).

3. The method according to claim 2, further comprising calculating an inversion delay time based on an average value of T1 within the said ROI such that the MR contrast image displays the ROI as black.

4. The method according to claim 2, further comprising calculating a repetition time, TR, and flip angle, α, based on an average value of T1 within the ROI such that the MR contrast image displays the ROI with optimal Signal to Noise Ratio, SNR.

5. The method according to claim 1, wherein said user-controlled marker represents a first region of interest (ROI), the method further comprising:
    marking a second region of interest (ROI), and
    displaying the MR contrast image representing the contrast image corresponding to the greatest difference in contrast between the first ROI and the second ROI.

6. The method according to claim 1, wherein a movement of said user-controlled marker in a first direction represents a change of T1 weighted contrast in the displayed MR contrast image.

7. The method according to claim 1, wherein a movement of said user-controlled marker in a second direction represents a change of T2 weighted contrast in the displayed MR contrast image.

8. The method according to claim 1, wherein the PD parameter is set such that the measured proton density appears to be uniform over the image, in order to abolish the PD contrast.

9. The method according to claim 1, wherein the influence of the T1 parameter is inverted, in order to make the contrast due to T1 weighting behave similarly like the contrast due to T2 weighting.

10. The method according to claim 1, wherein the T1 parameter or a mathematical function thereof, T2 parameter or a mathematical function thereof, and PD parameter or a function thereof span a three-dimensional space with computed values of the tissue parameters set as coordinates.

11. The method according to claim 10, where the parameters or functions thereof spanning the three-dimensional space are selected such that computed values for similar tissue will form clusters in the visualized three dimensional space and each cluster represents a similar tissue type.

12. The method according to claim 11, wherein a normalized distance in the three-dimensional space between clusters corresponds to a partial volume of the respective tissue type in relation to other clusters.

13. The method according to claim 1, wherein a 'disease image' is generated by subtracting an image with an amount of recognized healthy tissue from the MR contrast image.

14. A device for visualizing magnetic resonance (MR) images on a screen, comprising:
    a memory for storing scanned MR images having various contrast,
    a computing unit configured to compute values for the parameters T1 relaxation time, T2 relaxation time, and proton density (PD) or a subset of those parameters for a set of scanned MR images, the subset including at least one of each of T1 relaxation time, T2 relaxation time, and proton density PD,
    an MR contrast image generation unit configured to generate an MR contrast image using the scanned MR images, values computed, and a set of default scanner settings, and
    an MR contrast image updating unit configured to adjust the image contrast of said MR contrast image by changing scanner settings in response to a user-controlled marker on said screen.

15. The device according to claim 14, wherein said user-controlled marker represents a region of interest (ROI).

16. The device according to claim 14, wherein the device is configured for calculating an inversion delay time based on an average value of T1 within the ROI.

17. The device according to claim 14, wherein the device is configured for calculating a repetition time, TR, and flip angle, α, based on an average value of T1 within the ROI.

18. The device according to claim 14, wherein two user-controlled markers represent a first region of interest (ROI), and a second region of interest (ROI), the device being configured to display the MR contrast image representing the contrast image corresponding to the greatest difference in contrast between the first ROI and the second ROI.

19. The device according to claim 14, wherein the device is configured to interpret a movement of said user-controlled marker in a first direction as a request for a change of T1 weighted contrast in the displayed MR contrast image.

20. The device according to claim 14, wherein the device is configured to interpret a movement of said user-controlled marker in a second direction as a request for a change of T2 weighted contrast in the displayed MR contrast image.

21. The device according to claim 14, wherein the device is configured to set the normalization of the PD parameter such that the measured proton density appears to be uniform over the image.

22. The device according to claim 14, wherein the device is configured to use the T1 parameter or a mathematical function thereof, T2 parameter or a mathematical function thereof, and PD parameter or a function thereof to span a three-dimensional space with computed values of the tissue parameters set as coordinates.

23. The device according to claim 22, where the parameters or functions thereof spanning the three-dimensional space are selected such that computed values for similar tissue will form clusters in the visualized three dimensional space and each cluster represents a similar tissue type.

24. The device according to claim 23, wherein the device is configured such that a normalized distance in the three-dimensional space between clusters corresponds to a partial volume of the respective tissue type in relation to other clusters.

25. The device according to claim 14, wherein the device is configured to generate a disease image by subtraction of an image of recognized healthy tissue from the MR contrast image.

26. A Magnetic Resonance Imaging (MRI) system comprising a device in accordance with claim 14.

27. A non-transitory computer program product comprising program segments that when executed by a computer causes the computer to perform the steps of:
    loading scanned Magnetic Resonance (MR) images having various contrast
    computing values for the parameters T1 relaxation time, T2 relaxation time, and proton density (PD) for the loaded scanned MR images or a subset of those parameters, the subset including at least one of each of T1 relaxation time, T2 relaxation time, and proton density PD,
    generating an MR contrast image using the scanned MR images, the computed values, and a set of default scanner settings and
    adjusting the image contrast of said MR contrast image by changing scanner settings in response to a user-controlled marker on said screen.

28. A method of visualizing a magnetic resonance (MR) image, the method comprising the steps of:
    scanning MR images having various contrast,
    computing values for the parameters T1 relaxation time, T2 relaxation time, and proton density (PD) for the scanned MR images or a subset of those parameters, the subset including at least one of each of T1 relaxation time, T2 relaxation time, and proton density PD,
    generating an MR contrast image based on the scanned MR images having various contrast, computed values, and a set of default scanner settings,
    generating a vector dependent on at least two of the T1 relaxation time, T2 relaxation time, and proton density (PD) parameters of the generated MR contrast image, and
    displaying the absolute value of the vector.

29. A device for visualizing a magnetic resonance (MR) image comprising:
    means for scanning MR images having various contrasts,
    means for computing absolute values for the parameters T1 relaxation time, T2 relaxation time, and proton density (PD) for the scanned MR images or a subset of those parameters, the subset including at least one of each of T1 relaxation time, T2 relaxation time, and proton density (PD),
    means for generating an MR contrast image based on the scanned MR images having various contrasts, computed values, and a set of default scanner settings,
    means for generating a vector dependent on at least two of the T1 relaxation time, T2 relaxation time, and proton density (PD) parameters of the MR contrast image, and
    means for displaying the absolute value of the vector.

30. A method of visualizing magnetic resonance (MR) images on a screen, the method comprising the steps of:
    scanning MR images having various contrast,
    computing values for the parameters T1 relaxation time, T2 relaxation time, and proton density (PD) for the scanned MR images or a subset of those parameters, the subset including at least one of each of T1 relaxation time, T2 relaxation time, and proton density PD,
    setting the PD to a value equal for all tissue in the scanned MR images, and
    generating an MR contrast image using the scanned MR images, the computed values of T1 relaxation time and T2 relaxation time, and the set PD.

31. The method according to claim 30, wherein the MR contrast image is a pure T1 weighted contrast or a pure T2 contrast image.

32. The method according to claim 30, wherein the MR contrast image is a mixed T1 and T2 weighted contrast image.

33. A device for visualizing magnetic resonance (MR) images on a screen, comprising:
    means for scanning MR images having various contrast,
    means for computing values for the parameters T1 relaxation time, T2 relaxation time, and proton density (PD) for the scanned MR images or a subset of those parameters, the subset including at least one of each of T1 relaxation time, T2 relaxation time, and proton density PD,
    means for setting the PD to a value equal for all tissue in the scanned MR images, and
    means for generating an MR contrast image using the scanned MR images, the computed values of T1 relaxation time and T2 relaxation time, and the set PD.

34. The method according to claim 33, wherein the MR contrast image is a pure T1 weighted contrast or a pure T2 contrast image.

35. The method according to claim 33, wherein the MR contrast image is a mixed T1 and T2 weighted contrast image.

* * * * *